United States Patent [19]

Maki

[11] Patent Number: 5,755,728

[45] Date of Patent: May 26, 1998

[54] SUTURE APPARATUS WITH LOOP END PORTIONS

[76] Inventor: Neil J. Maki, 403 Canal St., Thibodaux, La. 70301

[21] Appl. No.: 611,591

[22] Filed: Mar. 7, 1996

[51] Int. Cl.$^6$ .................................................. A61B 17/04
[52] U.S. Cl. ........................ 606/145; 606/145; 606/139; 606/144; 606/148
[58] Field of Search ...................... 606/139, 144, 606/145, 146, 148; 112/169

[56] References Cited

U.S. PATENT DOCUMENTS

| | | |
|---|---|---|
| 3,125,095 | 3/1964 | Kaufman et al. . |
| 3,570,497 | 3/1971 | Lemole . |
| 3,580,256 | 5/1971 | Wilkinson et al. . |
| 4,441,497 | 4/1984 | Paudler . |
| 4,890,615 | 1/1990 | Caspari et al. . |
| 4,923,461 | 5/1990 | Caspari et al. . |
| 4,950,283 | 8/1990 | Dzubow et al. . |
| 5,222,976 | 6/1993 | Yoon . |
| 5,250,053 | 10/1993 | Snyder . |
| 5,282,809 | 2/1994 | Kammerer et al. ............ 606/148 |
| 5,312,436 | 5/1994 | Coffey et al. . |
| 5,403,331 | 4/1995 | Chesterfield et al. .......... 606/148 |
| 5,403,346 | 4/1995 | Loeser ............................ 606/228 |
| 5,454,834 | 10/1995 | Boebel et al. .................. 606/230 |
| 5,466,241 | 11/1995 | Leroy et al. .................... 606/139 |
| 5,489,288 | 2/1996 | Buelna ............................ 606/144 |
| 5,562,684 | 10/1996 | Kammerer ..................... 606/139 |
| 5,571,120 | 11/1996 | Yoon .............................. 606/148 |

OTHER PUBLICATIONS

Linvatec 1994 Product Catalog, p. 50, Inteq "Small Joint Suturing System".
Linvatec 1994 Product Catalog, p. 56, Shuttle–Relay Suture Passer.
Linvatec 1994 Product Catalog, p. 59, Hawkeye Suture Needle.

*Primary Examiner*—Michael Buiz
*Assistant Examiner*—Tina T.D. Pham
*Attorney, Agent, or Firm*—Pravel, Hewitt, Kimball & Krieger

[57] ABSTRACT

A method of transporting suture materials deep within a patient's body cavity includes the providing of an elongated instrument having proximal and distal end portions and an elongated continuous bore with an internal diameter of about one millimeter or less. The elongated instrument is provided for gripping and transporting a length of suture material that is placed within the bore. The elongated length of suture shuttle material is placed in the bore, the shuttle having loops at each end. Each loop includes a short leader portion that is a single strand monofilament member at the end of the shuttle. The surgeon can then move the shuttle material and its loops through the bore after pushing a sharp end of the instrument through tissue to be sutured. The shuttle is then thrusted through the instrument and through the selected tissue until one or both of the loops passes through the instrument bore and the tissue. This allows the surgeon to add suture to either one of the loops either before or after being transported through the bore of the instrument.

12 Claims, 3 Drawing Sheets

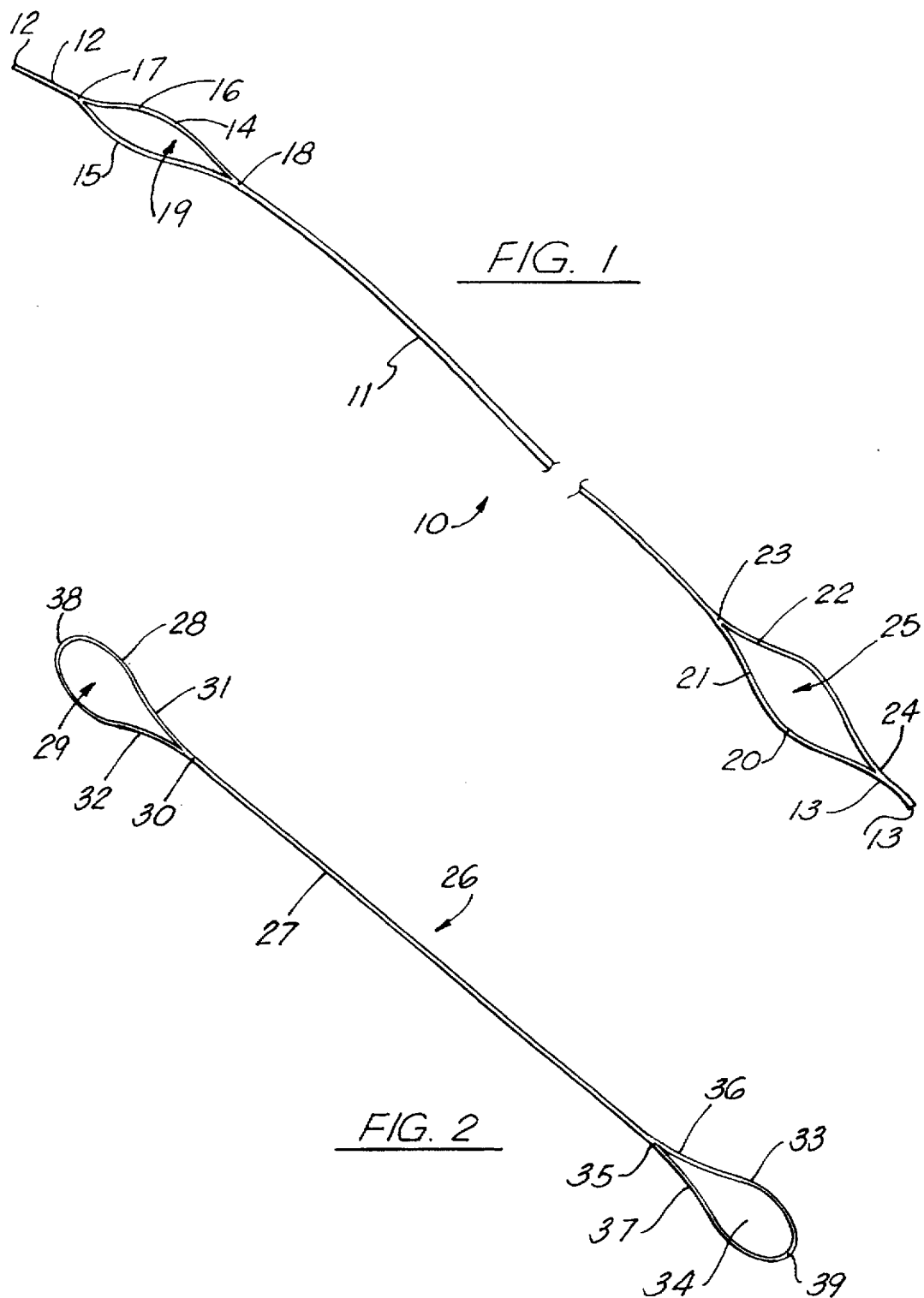

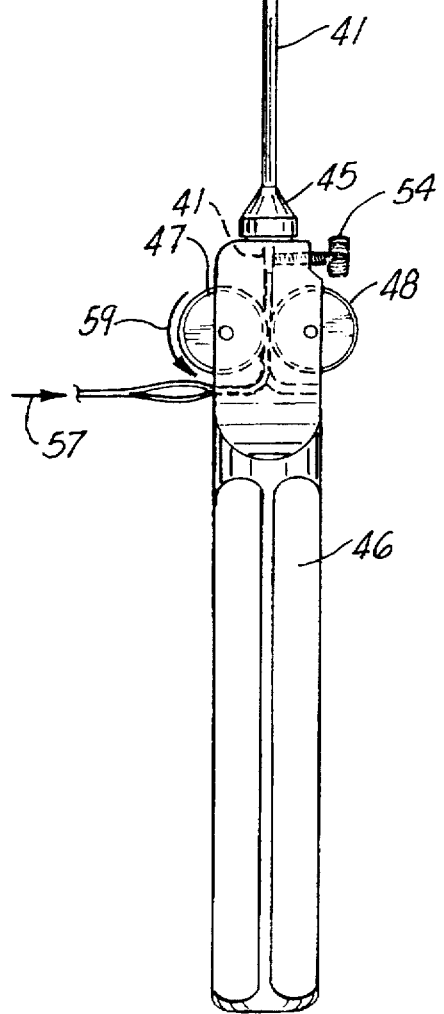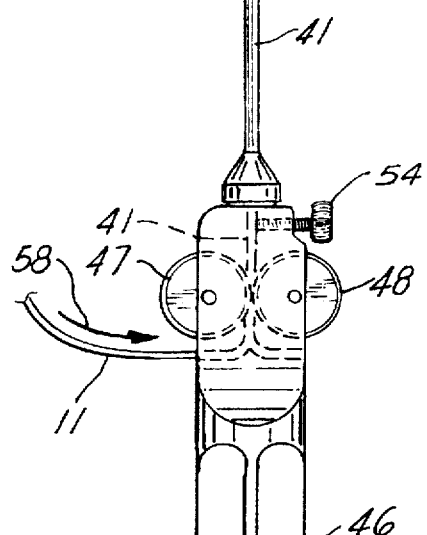

SUTURE APPARATUS WITH LOOP END PORTIONS

BACKGROUND OF THE INVENTION

1. Field of the Invention

The present invention relates to surgical sutures, and more particularly relates to an improved surgical suture shuttle device and related surgical technique. Even more particularly, the present invention relates to an improved surgical suture device in the form of a suture shuttle that is transported to or from a tissue site through a roller-type suture passing device.

2. General Background

Surgical sutures are used to join together portions of tissue as part of a medical procedure. Sutures can be provided with needles at one or both ends of the suture. Other types of suture are not provided with needles. These types of sutures can be added to a surgical needle through an eyelet portion.

Some sutures are placed in a desired position using a roller-type suture passing device. These instruments are typically thumb operated by the surgeon. By rotating the thumbwheels of such a roller-type suture passing device, the surgeon can either thrust the suture toward the patient's tissue or remove the suture from the patient's tissue.

The Paudler U.S. Pat. No. 4,441,497 is an example of such a suture passing device. U.S. Pat. Nos. 4,890,615 and 4,923,461 are later examples of suture passing devices that use one or more rollers to advance the suture or to withdraw the suture.

Suture passing devices are commercially available. One supplier of such commercially available devices is Linvatec Corporation of Largo, Fla. A small joint suture system that includes instruments to advance suture material is sold commercially under the trademark Inteq. Inteq literature states that U.S. Pat. Nos. 4,890,615 and 4,923,461 cover the Inteq small joint suturing system.

SUMMARY OF THE INVENTION

The present invention provides an improved method of transporting suture material to a location deep within a patient's body cavity.

The method of the present invention provides an elongated instrument having proximal and distal end portions and a cannula portion having an elongated continuous bore that is sized and shaped to transport a length of suture material that is positioned within the bore.

An elongated length of monofilament suture shuttle material is positioned within the bore, the suture shuttle material having loops at each end and each loop having a short leader portion that is a single monofilament strand located at the end of the suture shuttle material above the loop.

The shuttle material and its loops are moved through the bore wherein the end portions of the shuttle material and the collapsed loops are sized and shaped to travel through the bore.

A length of suture can be secured to the shuttle at one of the loops either before or after exiting the cannula bore. This allows the surgeon great flexibility in placing suture material at a desired location relative to tissue that is to be treated, sewn, tied, or the like.

In one embodiment, the instrument has a sharp end portion that can be placed through selected tissue to be sutured so that when the shuttle is transported the full length of the cannula, it exits the instrument distal end that has been pushed through the selected tissue.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 1 is a schematic perspective view of the suture passing device constructed in accordance with the present invention;

FIG. 2 is a schematic perspective view of a second embodiment of the suture passing device constructed in accordance with the present invention;

FIGS. 5 and 6 are schematic elevational views illustrating the method of the present invention during the transportation of the suture passing device of the present invention through a suture passing instrument.

DETAILED DESCRIPTION OF THE PREFERRED EMBODIMENT

Figure 3:
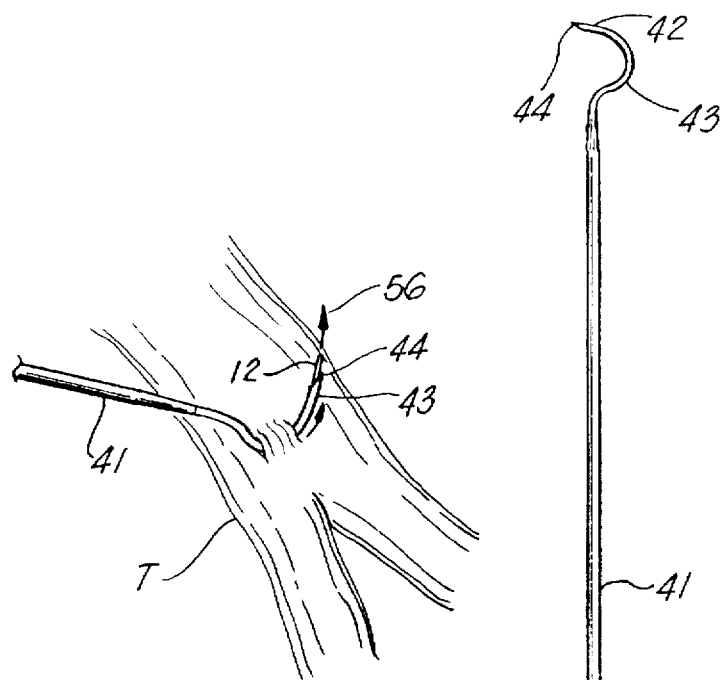
FIG. 3 is a schematic perspective view illustrating the method of the present invention.

FIG. 1 shows the preferred embodiment of the suture shuttle device of the present invention designated generally by the numeral 10. Suture shuttle device 10 is preferably entirely of non-metallic material such as a plastic or polymeric monofilament material, being sized and shaped to fit within a bore 53 of cannula 41 of suture passing instrument 40 of FIGS. 4–6. The bore 53 can be about 0.25–1.00 mm in diameter.

Shuttle device 10 includes an elongated central monofilament member 11, a pair of leader end portions 12, 13, and loops 14, 20 that are positioned in between the central elongated monofilament member 11 and the two end portions 12, 13. The loop 14 has a pair of loop segments 15, 16 that are of equal length. The loop segments 15, 16 extend from branch members 17, 18 providing an opening 19 in between the members 14 and 15. The loop segments 15 and 16 are of equal length and therefore can conform closely to one another so that the entire shuttle device 10 can be fed through an instrument such as suture passing instrument 40. In such a case, the surgeon feeds the shuttle device 10 through a selected passage 51 or 52 and into a hollow bore 53 of an elongated cannula 41.

In the embodiment of FIG. 1, there are a pair of monofilament leader end portions 12, 13 that are each about one-half inch in length. These leader end portions 12, 13 assist the surgeon in feeding the shuttle device 10 into the instrument 40. The embodiment of FIG. 1 is entirely of monofilament construction, including the end portions 12, 13 and the loops 14, 20 as well as the central elongated portion 11.

In FIG. 2, a second embodiment 26 of the suture shuttle device of the present invention is shown. In the embodiment of FIG. 2, the suture shuttle device 26 has loops 28, 33 but the short leader end portions of the embodiment of FIG. 1 have been eliminated. The suture shuttle device 26 has an elongated monofilament member 27 that is centrally located and a pair of end loops 28, 33. The loop 28 has an opening 29 defined by loop segments 31, 32 that extend from branch 30. The loop segments 31, 32 are integrally joined as a continuous member at 38 which defines the end of the suture shuttle device. similarly, a loop 33 has a loop opening 34 and a pair of loop segments 36, 37 that extend from branch 35. The loop end 39 is simply an integral connection of the loop segments 33, 34.

In order to feed the suture shuttle device 26 into an instrument 40, the surgeon simply closes the loop segments 31, 32 or the loop segments 36, 37 by aligning the selected loop segments 31, 32 or 36, 37 together. The surgeon then feeds an end 38 or 39 into a selected channel 51 or 52 of instrument 40 until the selected end 38 or 39 is gripped by thumbwheels 47, 48.

Figure 4:
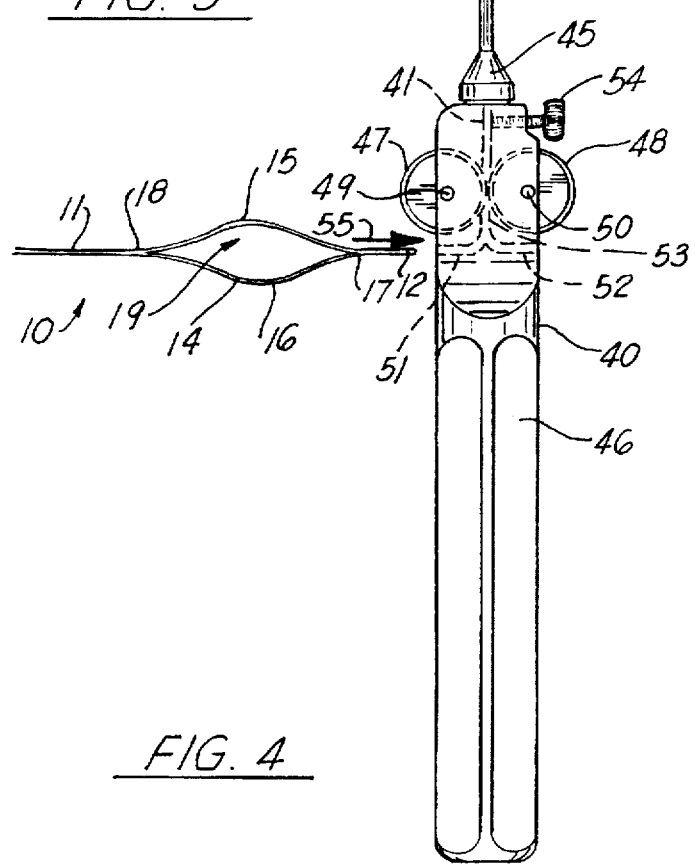
FIG. 4 is a perspective view illustrating another method step of the present invention wherein a suture passing device of the present invention is loaded into a suture passing instrument.

FIGS. 3–6 show the method of the present invention using a commercially available suture passing instrument 40. In FIG. 4, the instrument 40 includes an elongated cannula portion 41 that can be removably attached to the instrument 40 in a manner known in the art. Commercially available suture passing devices 40 can have a cannula 41 with a distal end 42 and an annular collar 45 that acts as a stop when the cannula 41 is attached to the instrument handle 46 using set screw 54.

Upon assembly of a selected cannula 41 to handle 46, the surgeon tightens the set screw 54 and uses the thumbwheels 47, 48 to transport a suture shuttle 10 or 26 to selected patient's tissue T. The surgeon uses the sharp end 14 of the end portion 42 to engage selected tissue T as shown in FIG. 3. Typically, such tissue is in a hard to reach location such as deep within a body cavity.

Once the surgeon has placed the distal end 42 of the cannula 41 through selected tissue T, the surgeon then feeds the shuttle device 10 or 26 into a selected channel 51 or 52 of the instrument 40. In FIG. 4, the end portion 12 is shown being fed into the channel 51 as indicated by arrow 55. Once the end 12 of the shuttle device 10 enters the passageway 51, the end portion 12 is gripped by the rollers 47, 48 as they rotate about axles 49, 50 (see FIG. 5).

In order to insert the shuttle device 10 into the bore 53 of cannula 41, the surgeon rotates the thumbwheels 47, 48 in the direction of arrow 59. This moves the shuttle 10 in the direction of arrow 57 through the bore 53 of cannula 41 from a location at collar 45 to the lower pointed tip 44. In the embodiment shown, the cannula 41 provides a continuous open ended bore that communicates with the channels 51, 52 and with the extreme end portion 42 of cannula 41 at tip 44. This allows the surgeon to transport the shuttle 10 to the tip 44 of cannula 41 so that the shuttle end 12 exits the cannula 41 at tip 44 as shown by the arrow 56 in FIG. 3.

Because the surgeon has loops at each end of the selected shuttle 10 or 26, the surgeon can place a length of suture to be transported into either of the loops 14 or 20 in the case of shuttle 10 or into either of the loops 28 or 33 in the case of shuttle 26. This affords great flexibility to the surgeon in placing sutures deep within a body cavity.

Because the shuttle provides loops at each end, the surgeon can add a length of suture to be transported before transporting the shuttle 10 or 26 via the instrument 40 to the body tissue T or can add a length of suture to the loop at one end of the shuttle 10 or 26 after it has passed through the tissue T as shown in FIGS. 3 and 6. In FIG. 6, the end portion 12 of shuttle 10 is shown having exited cannula 41 at the end 42 thereof. The opening 19 allows a surgeon to add a length of suture to that loop 14, for example, after the end portion 42 has been placed through selected tissue T as shown in FIG. 3.

The following table lists the parts numbers and parts descriptions as used herein and in the drawings attached hereto.

PARTS LIST

| Part Number | Description |
| --- | --- |
| 10 | suture shuttle device |
| 11 | monofilament member |
| 12 | end |
| 13 | end |
| 14 | loop |
| 15 | loop segment |
| 16 | loop segment |
| 17 | branch |
| 18 | branch |
| 19 | opening |
| 20 | loop |
| 21 | loop segment |
| 22 | loop segment |
| 23 | branch |
| 24 | branch |
| 25 | opening |
| 26 | suture passing device |
| 27 | monofilament member |
| 28 | loop |
| 29 | opening |
| 30 | branch |
| 31 | loop segment |
| 32 | loop segment |
| 33 | loop |
| 34 | opening |
| 35 | branch |
| 36 | loop segment |
| 37 | loop segment |
| 38 | end |
| 39 | end |
| 40 | suture passing instrument |
| 41 | cannula |
| 42 | distal end |
| 43 | curved portion |
| 44 | sharp tip |
| 45 | annular collar |
| 46 | handle |
| 47 | thumbwheel |
| 48 | thumbwheel |
| 49 | axle |
| 50 | axle |
| 51 | channel |
| 52 | channel |
| 53 | bore |
| 54 | set screw |
| 55 | arrow |
| 56 | arrow |
| 57 | arrow |
| 58 | arrow |
| 59 | arrow |
| T | tissue |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method of transporting suture material deep within a patient's body cavity comprising the steps of:

a) providing an elongated instrument having proximal and distal end portions and an elongated continuous bore sized and shaped to transport a length of suture material that is positioned in the bore;

b) placing an elongated suture shuttle of a flexible, non-metallic material in the bore, the suture shuttle having a central elongated single strand portion with loops at each end, and each loop having a short leader portion located at the end of the suture shuttle above the loop and generally opposite the central strand portion;

c) moving the shuttle and its loops through the bore beginning with a short leader portion, wherein the end portions of the shuttle material with the loops are sized and shaped to travel through the bore with the loops collapsed;

d) securing the length of suture to the shuttle at one of the loops;

e) placing the instrument distal end through tissue to be sutured; and f) thrusting the shuttle through the bore until a first loop passes completely through the bore and out the distal end.

2. The method of claim 1 wherein the bore is about 0.25–1.0 mm in diameter.

3. The method of claim 1 wherein the step "c" includes rotating said thumbwheel on said instrument to advance the shuttle.

4. The method of claim 1 wherein both loops travel through the bore exiting the distal end.

5. The method of claim 1 wherein step "b" includes providing an elongated suture shutter of monofilament material in the bore.

6. The method of claim 5 wherein step "b" includes providing an elongated suture shuttle of monofilament material having two loops at the end portions of the shuttle, each loop having a short leader that is many times shorter than the control elongated central strand portion, wherein the loops and each short leader are of a monofilament material.

7. The method of claim 6 wherein the monofilament is a plastic.

8. The method of claim 6 wherein the monofilament is polymeric.

9. The method of claim 1 wherein step "c" further comprises collapsing each loop within the bore so that the loops occupy a portion of the bore about equal to the portion of the bore occupied by the shuttle central portion.

10. A method of transporting suture material deep within a patient's body cavity comprising the steps of:

a) providing an elongated instrument having proximal and distal end portions and an elongated continuous bore sized and shaped to transport a length of suture material that is positioned in the bore;

b) placing an elongated suture shuttle of plastic monofilament material in the bore, the suture shuttle having a central elongated single strand portion that defines a majority of the length of the suture shuttle and a pair of loops at end portions of the central portion, each of the loops comprised of a pair of elongated loop sections of the same length that can collapse together and align when the suture shuttle occupies the instrument bore, and each loop has a single strand short leader monofilament positioned on the loop opposite the central strand portion.

c) moving the shuttle material and its loops through the bore, wherein the end portions of the shuttle material with the loops are sized and shaped to travel through the bore with the loops collapsed;

d) securing the length of suture to the shuttle at one of the loops;

e) placing the instrument distal end through tissue to be sutured; and f) thrusting the shuttle through the bore until a first loop passes completely through the bore and out the distal end.

11. The method of claim 10 further comprising the step between "b" and "c" of using rotary wheels mounted on the instrument at the bore to engage and move the suture shuttle.

12. The method of claim 10 wherein the shuttle has a short monofilament leader at each loop and further comprising the step between steps "b" and "c" of using rotary wheels mounted on the instrument at the bore to engage and move the suture shuttle.

\* \* \* \* \*